(12) United States Patent
Partlett

(10) Patent No.: US 8,251,977 B2
(45) Date of Patent: Aug. 28, 2012

(54) CATHETER STEERING SYSTEM

(75) Inventor: Matthew J. Partlett, Allawah (AU)

(73) Assignee: Cathrx Ltd, Homebush Bay (AU)

( * ) Notice: Subject to any disclaimer, the term of this patent is extended or adjusted under 35 U.S.C. 154(b) by 128 days.

(21) Appl. No.: 11/983,238

(22) Filed: Nov. 7, 2007

(65) Prior Publication Data
US 2008/0140053 A1 Jun. 12, 2008

Related U.S. Application Data

(60) Provisional application No. 60/861,642, filed on Nov. 28, 2006.

(51) Int. Cl.
*A61M 25/00* (2006.01)
(52) U.S. Cl. ............... 604/525; 604/523; 604/524
(58) Field of Classification Search ............ 604/523, 604/525, 527, 528
See application file for complete search history.

(56) References Cited

U.S. PATENT DOCUMENTS

| | | | |
|---|---|---|---|
| 6,746,422 B1 | 6/2004 | Norlega et al. | |
| 2001/0049519 A1* | 12/2001 | Holman et al. | 604/534 |
| 2002/1082584 | 6/2002 | Rosenman et al. | |
| 2003/0125709 A1* | 7/2003 | Eidenschink | 604/524 |
| 2004/0039326 A1* | 2/2004 | Hata et al. | 604/19 |
| 2005/0288626 A1 | 12/2005 | Koerner et al. | |
| 2006/0184105 A1 | 8/2006 | Townsend et al. | |

FOREIGN PATENT DOCUMENTS

| | | |
|---|---|---|
| EP | 0 790 066 A2 | 8/1997 |
| EP | 0 790 066 A3 | 8/1997 |
| JP | 2004-351005 A | 12/2004 |
| WO | WO-97/27895 A1 | 8/1997 |
| WO | WO-2005/094477 A2 | 10/2005 |
| WO | WO-2005/094477 A3 | 10/2005 |
| WO | WO-2006/012668 A1 | 2/2006 |
| WO | WO-2006/065949 A2 | 6/2006 |
| WO | WO-2006-065949 A3 | 6/2006 |

OTHER PUBLICATIONS

European Search Report mailed Jul. 25, 2008, for EP Application No. 07254554.4, filed on Nov. 22, 2007, eight pages.
Notice of Reasons for Rejection mailed on Jul. 27, 2010, for Japanese Patent Application No. P2007-293528, filed on Dec. 11, 2007, four pages.

* cited by examiner

*Primary Examiner* — Kevin C Sirmons
*Assistant Examiner* — Brandy C Scott
(74) *Attorney, Agent, or Firm* — TraskBritt

(57) ABSTRACT

A catheter steering mechanism includes a tubular member defining a passage. The tubular member has a longitudinally extending cutaway portion defining a bend-enhancing region formed at a predetermined location along a length of the tubular member. An actuator is received in the passage of the tubular member, a distal part of the actuator being fast with a distal part of the tubular member. A restraining arrangement is defined by the tubular member, the restraining arrangement comprising a structure arranged at the bend-enhancing region to retain the actuator substantially within the confines of the tubular member during bending.

19 Claims, 2 Drawing Sheets

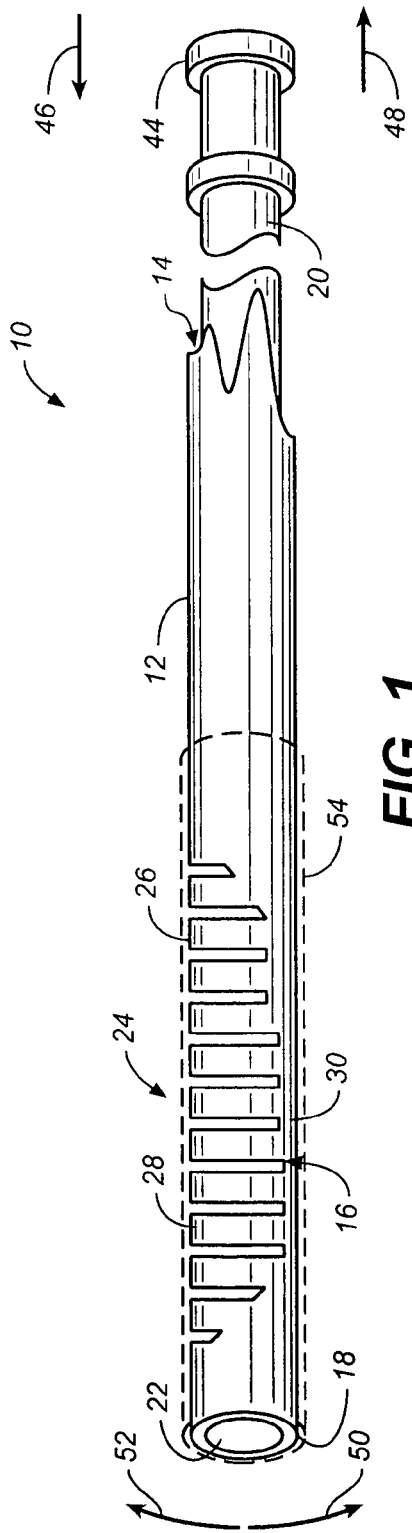
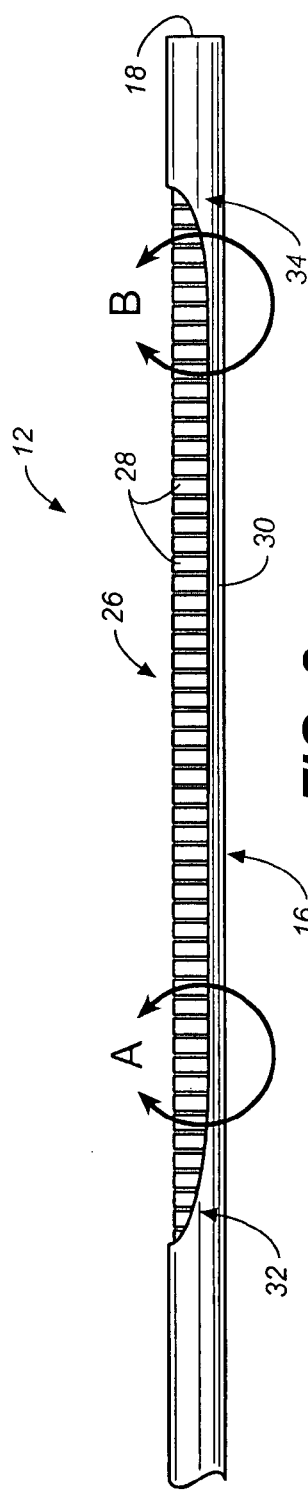
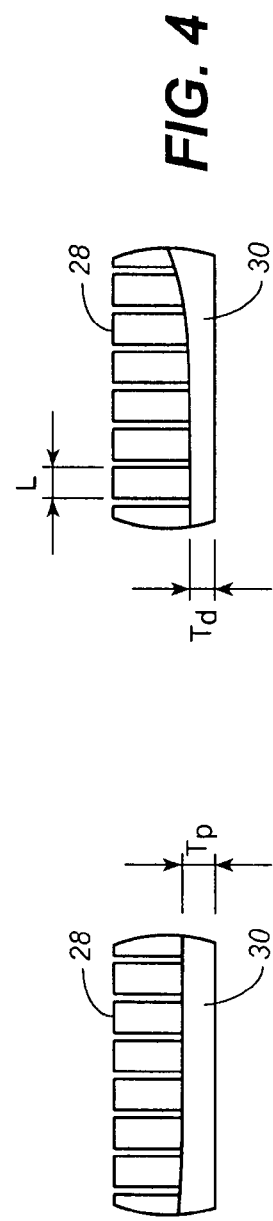
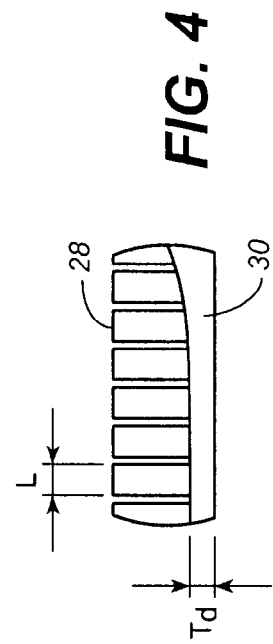
FIG. 1
FIG. 2
FIG. 3
FIG. 4

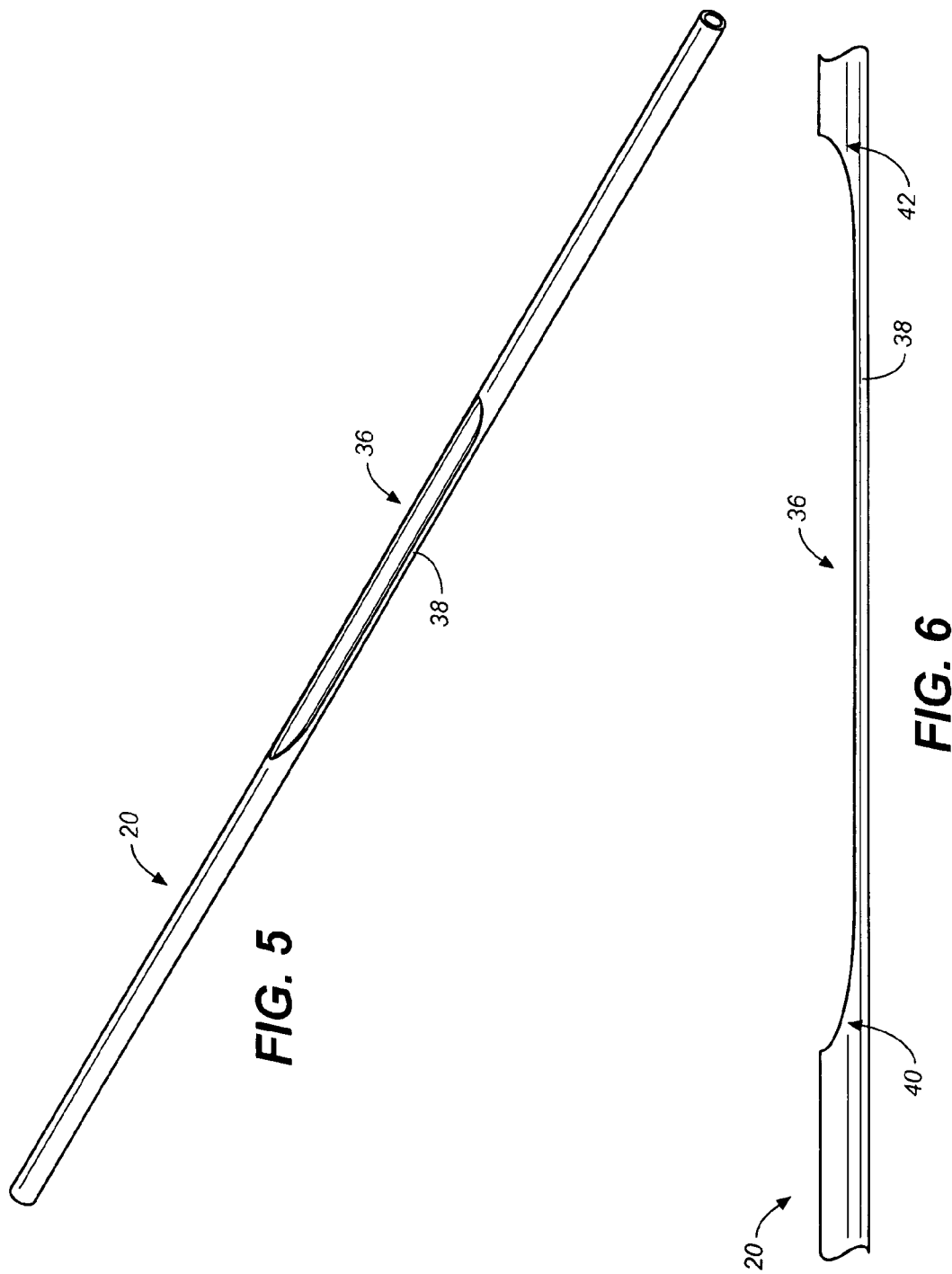

CATHETER STEERING SYSTEM

CROSS-REFERENCE TO RELATED APPLICATIONS

The present application claims priority from U.S. Provisional Application No. 60/861,642 filed on Nov. 28, 2006, the disclosure of which is incorporated herein by reference in its entirety.

FIELD

This invention relates, generally, to a catheter steering system and, more particularly, to a catheter steering mechanism and to a steerable catheter including the steering mechanism.

BACKGROUND

Electrophysiology catheters are medical devices used for measuring electrical signals within the heart and are often used in the diagnosis of various arrhythmias. Certain types of these catheters may also be used for treating arrhythmias through ablative techniques.

Generally, to access the region of the heart to be treated, the catheter is inserted through the femoral vein of the patient. The tip of the catheter is steered through the vascular system of the patient to the desired location. Similarly, the catheter tip is steered through the ventricles of the heart to arrive at the desired location.

Steerable catheters have, in the past, made use of a metal strip or shim contained within the distal end of the catheter as a portion of a steering device. One or more pull wires are connected to the metal strip. Manipulation of these pull wires causes the metal strip to bend to deflect the distal end of the catheter.

Such a design is complex and difficult to manufacture. In particular, the numerous components must be assembled and joined together, typically by hand.

In addition, a catheter lumen often contains a steering device along with other elements such as electrical conductors. Therefore, space within the lumen is at a premium.

SUMMARY

According to a first aspect of the invention, there is provided a catheter steering mechanism, the steering mechanism including:

a tubular member defining a passage, the tubular member having a longitudinally extending, cutaway portion defining a bend-enhancing region formed at a predetermined location along a length of the tubular member;

an actuator received in the passage of the tubular member, a distal part of the actuator being fast with a distal part of the tubular member; and a restraining arrangement defined by the tubular member, the restraining arrangement comprising a structure arranged at the bend-enhancing region to retain the actuator substantially within the confines of the tubular member during bending.

The predetermined location of the bend-enhancing region is that part of the tubular member at which it is desired that bending is to occur.

The cutaway portion may subtend an angle greater than 180° of a wall of the tubular member to retain a longitudinally extending web or spine of material of the tubular member.

The cutaway portion may subtend a greater angle at a distal region of the cutaway portion than at a proximal region of the cutaway portion.

The cutaway portion may have radiused proximal and distal transition regions for stress relief purposes. The proximal transition region may have a greater radius than the distal transition region. With this arrangement of the transition regions, as well as by having a non-uniform width spine of material due to the differing amounts of material cut away from the proximal region and the distal region of the cutaway portion, more uniform bending of the tubular member is able to be achieved.

The actuator may have a region of reduced cross-section coincident with the bend enhancing region of the tubular member. The region of reduced cross-section may be defined by a cutaway portion of the actuator, the cutaway portion subtending an angle greater than 180° to retain a longitudinally extending web or spine of material of the actuator of a required final width.

When the actuator is received in the passage of the tubular member, the spine of the actuator may lie adjacent and in register with the spine of the tubular member.

As is the case with the tubular member, the cutaway portion of the actuator may subtend a greater angle at a distal region of the cutaway portion than at a proximal region of the cutaway portion.

The cutaway portion of the actuator may have radiused proximal and distal transition regions for stress relief purposes. The proximal transition region may have a greater radius than the distal transition region.

Preferably, the actuator is a rod. The term "rod" is to be understood in broad sense to include a wire, multi-strand cable, or the like.

The restraining arrangement may comprise a cage structure arranged at the bend enhancing region of the tubular member. The cage structure may comprise a plurality of spaced hoops arranged at longitudinally spaced intervals along the tubular member. Hoops may be arranged along the entire length of the bend enhancing region of the tubular member effectively to "fill" in the bend enhancing region apart from the gaps between the hoops. In this specification, the term "hoop" is to be understood as a substantially U-shaped element, i.e., not an endless element.

A length of each hoop may be greater than a spacing between adjacent hoops. The "length" of the hoop is its dimension parallel to a longitudinal axis of the tubular member.

The tubular member and the actuator may be of a superlastic material such as a nickel-titanium alloy material.

The actuator may be secured to a distal end of the tubular member at an attachment point with a part of the actuator extending distally of the attachment point. The part of the actuator extending distally of the attachment point may be shaped into a predetermined shape distally of the attachment point. Instead, a part of the tubular member may extend distally of the attachment point, the part of the tubular member extending distally of the attachment point being shaped into a predetermined shape distally of the attachment point.

A protective arrangement may be received over the tubular member to inhibit the ingress of foreign material into the tubular member. The protective arrangement may comprise a protective sheath received over the tubular member. The protective sheath may be a sleeve of a heat shrink material.

BRIEF DESCRIPTION OF THE DRAWINGS

FIG. 1 shows a schematic side view of an embodiment of a catheter steering mechanism;

FIG. 2 shows a side view of a first component of the catheter steering mechanism;

FIG. 3 shows, on an enlarged scale, a side view of the circled part of the first component marked "A" in FIG. 2;

FIG. 4 shows, on an enlarged scale, a side view of the circled part of the first component marked "B" in FIG. 2;

FIG. 5 shows a three dimensional view of a part of a second component of the catheter steering mechanism; and FIG. 6 shows a side view of a part of the second component.

DETAILED DESCRIPTION OF EXEMPLARY EMBODIMENT

In the drawings, reference numeral 10 generally designates a catheter steering mechanism in accordance with an embodiment of the invention. The catheter steering mechanism includes a tubular member 12 defining a passage 14. The tubular member 12 has a longitudinally extending cutaway portion 16 proximally of its distal end 18. The cutaway portion 16 defines a bend enhancing region in the tubular member 12. An elongate actuator 20 is received within the passage 14 of the tubular member 12. A distal end 22 of the actuator 20 is fast with the distal end 18 of the tubular member 12.

A restraining arrangement 24 is defined by the tubular member 12. The restraining arrangement 24 comprises a cage structure 26 arranged at the bend enhancing region 16 of the tubular member 12.

In this embodiment, the actuator 20 is a solid actuator but those skilled in the art will readily appreciate that the actuator could also be tubular.

Both the tubular member 12 and the actuator 20 of the steering mechanism 10 are formed of a suitable resiliently flexible material such as, for example, a superlastic material such as Nitinol.

Referring now to FIGS. 2 through 4, the tubular member 12 is described in greater detail. It is to be noted that the cage structure 26 comprises a plurality of longitudinally spaced hoops 28. The hoops 28 serve to constrain the actuator 20 within the confines of the tubular member 12 in the region of the cutaway portion 16 during bending of the tubular member 12.

The cutaway portion 16 subtends an angle exceeding 180°. This leaves a spine 30 of material to form a hinge about which the tubular member 12 can bend, in use. The spine 30 tapers towards the distal end of the bending enhancing region so that less material is present in the spine 30 at the distal end than at the proximal end of the spine 30. Thus, as shown in FIG. 3 of the drawings, a thickness $T_p$ at the proximal end of the spine 30 is greater than a thickness $T_d$ at the distal end of the spine 30. For example, the tubular member 12 may have an outer diameter of approximately 0.66 mm and an inner diameter of about 0.51 mm. The proximal thickness $T_p$ of the spine 30 is about 0.25 mm while the distal thickness $T_d$ of the spine 30 is about 0.15 mm.

Further, as illustrated in FIG. 2 of the drawings, the spine 30 has a radiused proximal transition 32 and a radiused distal transition 34 for stress relief purposes. The proximal transition 32 is longer than the distal transition 34 as a result of the proximal transition 32 having a greater radius than the distal transition 34. For a tubular member 12 having the dimensions given above, the proximal transition 32 is approximately 10 mm in length with the distal transition 34 having a length of approximately half of that, i.e., about 5 mm.

These dimensions, i.e., of the proximal transition 32, the distal transition 34, the proximal thickness $T_p$ and the distal thickness $T_d$, provide improved uniformity of bending of the tubular member 12 in the bend enhancing region defined by the cutaway portion 16 of the tubular member 12.

The actuator 20 is formed of a machined Nitinol wire having an outer diameter of about 0.47 mm to fit within the passage 14 of the tubular member 12. A part of the actuator 20 is shown in greater detail in FIGS. 5 and 6 of the drawings.

The actuator 20 has a cutaway portion 36 defining a spine 38 of material. In use, the actuator 20 is inserted into the passage 14 of the tubular member 12 with the spine 38 of the actuator 20 being in register, and coincident, with the spine 30 of the tubular member 12.

As is the case with the tubular member 12, the spine 38 of the actuator 20 has a proximal transition region 40 and a distal transition region 42. Once again, the proximal transition region 40 has a larger radius than the distal transition region 42. For example, the proximal transition region 40 may have a length of approximately 10 mm with the distal transition region 42 having a length of approximately half of that, i.e., about 5 mm.

Further, the spine 30 has a proximal thickness which is greater than the distal thickness. The proximal thickness of the spine 38 is, for example, about 0.22 mm while the distal thickness is about 0.16 mm. This, once again, improves the uniformity of bending of the steering mechanism 10.

The cage structure 26 of the restraining arrangement 24 is, as described above, made up of the longitudinally spaced hoops 28. In the embodiment illustrated the hoops 28 have a longitudinal length, L, exceeding that of the spacing between adjacent hoops 28. It will, however, be appreciated that this need not be the case and the spacing between the hoops 28 could be the same as, or greater than, the length, L, of the hoops 28 so long as the actuator 20 is constrained within the tubular member 12 at the region of the cutaway portion 16 during bending of the steering mechanism 10.

While not clearly illustrated in the drawings, it will also be understood that, where edges of the hoops 28 meet the spine 30, the edges are radiused so that the effects of localised stresses are reduced.

The restraining arrangement 24 is formed by laser cutting slots between the hoops 28 into the wall of the tubular member 12. This also forms the bend-enhancing region of the tubular member 12. Similarly, the cutaway portion 36 of the actuator 20 is formed by laser cutting.

In use, the actuator 20 is inserted into the passage 14 of the tubular member 12 and the distal end 18 of the tubular member 12 is secured to the distal end 22 of the tubular member 12, for example, by crimping, welding, or the like. A proximal end (not shown) of the tubular member 12 is fixed in position in a catheter handle and a proximal end 44 (FIG. 1) of the actuator 20 is longitudinally displaceably secured within the catheter handle to be displaceable in the direction of arrows 46 and 48. It will be appreciated that, if desired, the actuator 20 could be anchored and the tubular member 12 is then displaceably arranged relative to the actuator 20. What is required is relative longitudinal displacement between the tubular member 12 and the actuator 20.

When the actuator 20 is urged in the direction of arrow 46 relative to the tubular member 12, the steering mechanism 10 bends in the direction of arrow 50. Conversely, when the actuator 20 is pulled in the direction of arrow 48 relative to the tubular member 12, the steering mechanism 10 bends in the direction of arrow 52.

If desired, to inhibit the ingress of foreign material into the passage 14 of the tubular member 12, at least the distal end of the steering mechanism 10, containing the cutaway portion 16 of the tubular member 12, is covered with a protective sheath 54. The protective sheath 54 is, for example, a sleeve of a heat shrink material.

It is an advantage of the invention that, with the restraining arrangement 24, the actuator 20 is constrained within the tubular member 12 in the bend-enhancing region of the steering mechanism 10. The hoops 28 serve to provide this restraint. However, the hoops 28 are so arranged that the bending of the steering mechanism 12 in the region of the bend-enhancing region 16 is not adversely affected. In addition, the use of the restraining arrangement 24 improves the strength and durability of the steering mechanism 10 resulting in less likelihood of mechanical failure of the steering mechanism 10 in the bend-enhancing region of the tubular member 12.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

The invention claimed is:

1. A catheter steering mechanism, the steering mechanism including:
   a tubular member defining a passage, the tubular member having an elongate, longitudinally extending, cutaway portion defining a bend-enhancing region formed at a predetermined location along a length of the tubular member, the cutaway portion having radiused proximal and distal transition regions for stress relief purposes with the proximal transition region having a greater radius than the distal transition region so that the proximal transition region is longer, in the longitudinal direction of the tubular member, than the distal transition region;
   an actuator received in the passage of the tubular member to be co-axial with the tubular member, a distal part of the actuator being fast with a distal part of the tubular member; and
   a restraining arrangement defined by the tubular member, the restraining arrangement comprising a structure arranged at the bend-enhancing region to retain the actuator substantially within the confines of the tubular member during bending, such that applying a longitudinal force to the actuator applies a force to the tubular member, due to the respective distal ends of the actuator and tubular member being fast with one another, and causes a bending of the actuator and tubular member at the bend-enhancing region of the tubular member to steer a catheter in a desired lateral direction.

2. The mechanism of claim 1, in which the cutaway portion subtends an angle greater than 180° of a wall of the tubular member to retain a longitudinally extending web or spine of material of the tubular member.

3. The mechanism of claim 2, in which the cutaway portion subtends a greater angle at a distal region of the cutaway portion than at a proximal region of the cutaway portion.

4. The mechanism of claim 1, in which the actuator has a region of reduced cross-section coincident with the bend-enhancing region of the tubular member.

5. The mechanism of claim 4, in which the region of reduced cross-section is defined by a cutaway portion of the actuator, the cutaway portion subtending an angle greater than 180° to retain a longitudinally extending web or spine of material of the actuator.

6. The mechanism of claim 5, in which, when the actuator is received in the passage of the tubular member, the spine of the actuator lies adjacent and in register with the spine of the tubular member.

7. The mechanism of claim 5, in which the cutaway portion of the actuator subtends a greater angle at a distal region of the cutaway portion than at a proximal region of the cutaway portion.

8. The mechanism of claim 5, in which the cutaway portion of the actuator has radiused proximal and distal transition regions for stress relief purposes.

9. The mechanism of claim 8, in which the proximal transition region has a greater radius than the distal transition region.

10. The mechanism of claim 4, in which the actuator is a rod.

11. The mechanism of claim 1, in which the restraining arrangement comprises a cage structure arranged at the bend-enhancing region of the tubular member.

12. The mechanism of claim 11, in which the cage structure comprises a plurality of spaced hoops arranged at longitudinally spaced intervals along the tubular member.

13. The mechanism of claim 12, in which a length of each hoop is greater than a spacing between adjacent hoops.

14. The mechanism of claim 1, in which the tubular member and the actuator are of a superlastic material.

15. The mechanism of claim 1, in which the actuator is secured to a distal end of the tubular member at an attachment point with a part of the actuator extending distally of the attachment point.

16. The mechanism of claim 15, in which the part of the actuator extending distally of the attachment point is shaped into a predetermined shape distally of the attachment point.

17. The mechanism of claim 1, in which the actuator is secured to a distal end of the tubular member at an attachment point, with a part of the tubular member extending distally of the attachment point, the part of the tubular member extending distally of the attachment point being shaped into a predetermined shape distally of the attachment point.

18. The mechanism of claim 1, which includes a protective arrangement received over the tubular member to inhibit the ingress of foreign material into the tubular member.

19. The mechanism of claim 18, in which the protective arrangement comprises a protective sheath received over the tubular member.

* * * * *